(12) United States Patent
Narita et al.

(10) Patent No.: US 7,115,412 B2
(45) Date of Patent: Oct. 3, 2006

(54) PROCESS FOR THE PREPARATION OF OPTICALLY ACTIVE 7-SUBSTITUTED-3-(2-AMINOPROPYL)INDOLE DERIVATIVES AND INTERMEDIATES THEREFOR

(75) Inventors: Takao Narita, Zama (JP); Kunihiro Toyoda, Iwata (JP); Yoichiro Hirose, Yokohama (JP); Toshio Tsuchida, Yamato (JP); Shiro Kato, Sakai (JP); Hiroshi Harada, Suita (JP); Akihito Fujii, Ikoma (JP)

(73) Assignees: Mercian Corporation, Tokyo (JP); Dainippon Pharmaceutical Co., Ltd., Osaka (JP)

( * ) Notice: Subject to any disclaimer, the term of this patent is extended or adjusted under 35 U.S.C. 154(b) by 278 days.

(21) Appl. No.: 10/240,844

(22) PCT Filed: Mar. 30, 2001

(86) PCT No.: PCT/JP01/02762

§ 371 (c)(1),
(2), (4) Date: Dec. 6, 2002

(87) PCT Pub. No.: WO01/75137

PCT Pub. Date: Oct. 11, 2001

(65) Prior Publication Data

US 2003/0181732 A1    Sep. 25, 2003

(30) Foreign Application Priority Data

Apr. 4, 2000   (JP) .............................. 2000-102050

(51) Int. Cl.
*C12P 41/00*    (2006.01)

(52) U.S. Cl. .................. 435/280; 435/108; 435/170; 435/171; 435/169

(58) Field of Classification Search ................ 435/108, 435/170, 171, 169, 280
See application file for complete search history.

(56) References Cited

OTHER PUBLICATIONS

Eich et al., Herba Hungarica (1968), 7(2-3), 91-103.*
Brewster et al., "Organic Chemistry" 3rd Edition, Prentice Hall, Inc. 1961, pp. 219-220.*
K. Helen Ekborg Ott, et al., "Highly Enantioselective HPLC Separations Using the Covalently Bonded Macrocyclic Antibiotic, Ristocetin A, Chiral Stationary Phase", Chirality, vol. 10, No. 5, pp. 434 to 483, 1998.
Jhon C. Gebler et al., "Dimethylallyltryptophan Synthase. An Enzyme-Catalyzed Electrophilic Aromatic Substitution", J. Am. Chem. Soc., vol. 114, No. 19, pp. 7354-7360, 1992.
E.M.M. Van Den Berg et al., "Chemo-enzymic synthesis and characterization of L-tryptophan selectively 13C-enriched or hydroxylated in the six-membered ring using transformed *Escherichia coli* cells", Recueil Des Travaux Chimiques Des Pays-Bas, 109(4), pp. 287-297, XP002082902, 1990.

* cited by examiner

*Primary Examiner*—Irene Marx
(74) *Attorney, Agent, or Firm*—Wenderoth, Lind & Ponack, L.L.P.

(57) ABSTRACT

Disclosed are a process for preparation of an optically active 7-substituted 3-(2-aminopropyl)indole compound and an intermediate therefor. In the above preparation process, 7-substituted indole is reacted with L- or DL-serine in the presence of a tryptophan-synthesizing enzyme originating in microorganisms to form corresponding 7-substituted L-tryptophan, and it is subjected, if necessary, to reduction, protection, exchange and elimination.

5 Claims, No Drawings

PROCESS FOR THE PREPARATION OF OPTICALLY ACTIVE 7-SUBSTITUTED-3-(2-AMINOPROPYL)INDOLE DERIVATIVES AND INTERMEDIATES THEREFOR

TECHNICAL FIELD

The present invention relates to a process for preparation of an optically active 7-substituted-3-(2-aminopropyl)indole compound and an intermediate therefor. The above indole compound can be obtained by using as a starting material, 7-substituted-tryptophan prepared by reacting 7-substituted indole with L-serine in the presence of a microorganism or a cell lyzate thereof.

BACKGROUND ART

Many of compounds out of indole derivatives are under development as medicines since they have a very interesting biological activity, or some compounds have already been used as medicines.

Such derivatives include a drug represented by a formula:

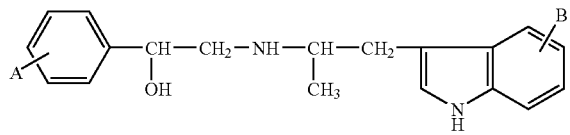

(wherein A and B represent at least one substituent including a hydrogen atom) which acts on each subclass of β-adrenergic receptor (WO96/16938, J. Med. Chem., 25, p. 670 to 679 (1982), British Patent No. 861,428 and the like). Carbon at a 2-position of a 2-aminopropane part bonded to a 3-position of an indole ring in these compounds is an asymmetric center, and plural stereoisomers originating therein can be present. However, specific isomers in these compounds are desirable in terms of a biological activity in many cases as commonly observed in biologically active substances. In actuality, a configuration at a 2-position in the part described above in a compound having a $β_3$-adrenergic receptor stimulation which is described in WO96/16938 is preferably either R- or S-. Accordingly, if it is intended to provide the indole derivative described above having a configuration in which the 2-aminopropane part described above is 2(R) or 2(S), the final compound or the synthetic intermediate having the 2-aminopropane part described above has to be subjected to optical resolution.

On the other hand, proposed in WO96/16938 is a method in which formed from a corresponding amine compound is a part of:

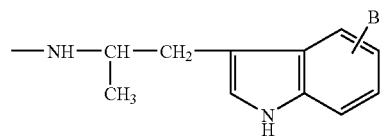

and in which formed from a corresponding oxirane compound or carboxylic acid compound is a part of:

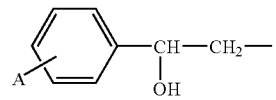

When employing such method, a desired optical isomer shall be able to be obtained as the final compound if the 2R- or 2S-isomer is used as the amine compound described above according to the purposes.

DISCLOSURE OF THE INVENTION

An object of the present invention is to provide 7-substituted indoles which are optically active amine compounds capable of being a synthetic intermediate of the indole derivative described in WO96/16938.

The present inventors have paid attentions as one means for achieving the object described above to applicability of L-tryptophan as a natural substance which has an indole skeleton and is provided with an optical activity. There has been proposed a wide variety of production processes for L-tryptophan such as a fermentation process using a producing microorganism thereof (for example, Japanese Patent Application Laid-Open No. 140891/1984) and a microbiological conversion process. In general, in the above conversion process, indole is reacted with L-serine or pyrubic acid under the action of a tryptophan synthase or a tryptophanase to produce L-tryptophan (for example, Japanese Patent Application Laid-Open No. 55188/1989, Japanese Patent Application Laid-Open No. 255082/1990, WO89/03428, Japanese Patent Application Laid-Open No. 103283/1996 and Japanese Patent Application Laid-Open No. 103284/1996). However, it is neither described nor indicated in these production processes for L-tryptophan whether or not these processes can be used for producing an L-tryptophan derivative having a substituent on an indole ring. On the other hand, known is a production process in which an indole derivative obtained by substituting with $CH_3$, $OCH_3$ or OH in any of a 2-, 4-, 5-, 6- and 7-positions of indole and DL-glyceric acid or glycerol are added to a fermentation broth of a bacterial strain such as a Corynebacterium genus and an Escherichia genus and reacted to produce an L-tryptophan derivative having a substituent corresponding to the above indole derivative (Japanese Patent Application Laid-Open No. 20392/1974).

If a carboxyl group of 7-substituted tryptophan out of these derivatives can efficiently be converted to the other group, various optically active 3- and 7-substituted indoles shall be able to be provided. When a carboxyl group is chemically converted to the other group, a stage for reducing the carboxyl group has to usually pass, and therefore it shall be necessary for conversion of the carboxyl group that a hydroxyl group at a 7-position of indole does not an adverse effect on such reduction reaction and that it is protected by a group which can readily and selectively be eliminated after prescribed reaction. A typical example of such protective group for a hydroxyl group includes a benzyl group.

The present inventors have found that 7-substituted indole having benzyloxy ($PhCH_2O$—) or diethylaminocarbonylmethoxy ($Et_2NCOCH_2O$—) at a 7-position which is a far more bulky group than a group of the indole derivative described in Japanese Patent Application Laid-Open No. 20392/1974, that is, $CH_3$, $OCH_3$ or OH can be converted to corresponding L-7-substituted tryptophan by using a tryptophan-synthesizing enzyme originating in microorganisms and that a carboxyl group of the above tryptophan can chemically be converted to the other various substituents at a good efficiency.

That is, the present invention is based on such knowledges.

Hence, according to the present invention, provided is a process for preparation of an optically active indole derivative of the Formula (I):

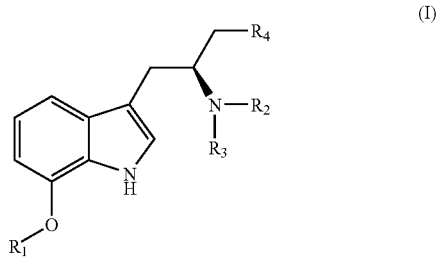

[wherein $R_1$ is a hydrogen atom, a lower alkyl group or a group selected from the following (a) and (b):

(a) a group of the formula —$(CH_2)_m$—$CHR_aR_{aa}$ (wherein $R_a$ is a hydrogen atom, a lower alkyl group, a lower alkoxycarbonyl group, a carboxyl group or a phenyl group which may be substituted (a substituent thereof is a lower alkyl group, a lower alkoxy group, a hydroxy group or a halogen atom); $R_{aa}$ is a lower alkoxycarbonyl group, a carboxyl group or a phenyl group which may be substituted (a substituent thereof is a lower alkyl group, a lower alkoxy group, a hydroxy group or a halogen atom); and m is an integer of 0 to 3) and (b) a group of the formula —$(CH_2)_p$—$R_b$ (wherein $R_b$ is a lower alkanoyl group, a hydroxy group, a cyano group or a mono- or di(lower alkyl)aminocarbonyl group, and p is an integer of 1 to 4); $R_2$ and $R_3$ are each a hydrogen atom, or either of them is a hydrogen atom and the other represents a lower alkanoyl group, a lower alkoxycarbonyl group or an aralkyloxycarbonyl group, or together form a phthaloyl group; and $R_4$ is a hydrogen atom, a halogen atom, a hydroxy group, a lower alkylsulfonyloxy group or a phenylsulfonyloxy group which may be substituted (a substituent thereof is a lower alkyl group, a lower alkoxy group or a halogen atom)], comprising the steps of:

a) reacting L- or DL-serine with 7-substituted indole of the Formula (II):

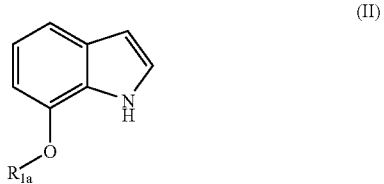

[wherein $R_{1a}$ is a group (c) or (d) shown below:

(c) a group of the formula —$(CH_2)_m$—$CHR_a'R_{aa}'$ (wherein $R_a'$ is a hydrogen atom, a lower alkyl group or a phenyl group which may be substituted (a substituent thereof is a lower alkyl group, a lower alkoxy group, a hydroxy group or a halogen atom); $R_{aa}'$ is a phenyl group which may be substituted (a substituent thereof is a lower alkyl group, a lower alkoxy group, a hydroxy group or a halogen atom); and m is an integer of 0 to 3) and (d) a group of the formula —$(CH_2)_p$—$R_b'$ (wherein $R_b'$ is a mono- or di(lower alkyl)aminocarbonyl group, and p is an integer of 1 to 4)] in the presence of a tryptophan-synthesizing enzyme originating in microorganisms to form 7-substituted-L-tryptophan of the Formula (III):

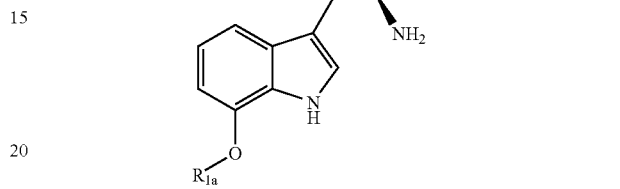

(wherein $R_{1a}$ is the same as described above), b) chemically reducing a carboxyl group of 7-substituted L-tryptophan of Formula (III) thus formed to a methylol group, c) protecting and modifying, if necessary, an amino group, d) turning, if necessary, a hydroxy group of methylol described above into sulfonyl to form a corresponding lower alkylsulfonyloxy compound or a phenylsulfonyloxy compound which may be substituted (a substituent thereof is a lower alkyl group, a lower alkoxy group or a halogen atom), e) halogenating it, if necessary, with alkali halide or halogenating a hydroxy group of methylol described above directly or in the presence of triphenylphosphine to form a corresponding halide, f) converting, if necessary, the sulfonyloxy compound or the halide obtained in d) or e) to methyl by hydrogenating in the presence of a palladium catalyst or using a metal hydride salt, g) eliminating, if necessary, the protective group of the amino group, and h) subjecting, if necessary, the substituent of $R_1$ to exchange reaction.

The compound of Formula (I) thus provided or a compound originating in the above compound is useful as a precursor or an intermediate of a bioactive substance. For example, when $R_2$ and $R_3$ in Formula (I) are hydrogen atoms, the final intended compound having a $\beta_3$-adrenergic receptor stimulation or a precursor thereof can be prepared by reaction with:

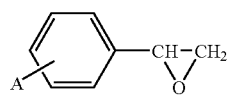

according to the process described in WO96/16938 described above.

Also, according to the present invention, provided is an optically active indole derivative of the Formula (IV):

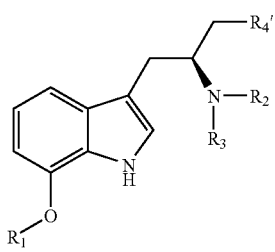

[wherein $R_1$ is a hydrogen atom, a lower alkyl group or a group selected from the following (a) and (b):
(a) a group of the formula —$(CH_2)_m$—$CHR_aR_{aa}$ (wherein $R_a$ is a hydrogen atom, a lower alkyl group, a lower alkoxycarbonyl group, a carboxyl group or a phenyl group which may be substituted (a substituent thereof is a lower alkyl group, a lower alkoxy group, a hydroxy group or a halogen atom); $R_{aa}$ is a lower alkoxycarbonyl group, a carboxyl group or a phenyl group which may be substituted (a substituent thereof is a lower alkyl group, a lower alkoxy group, a hydroxy group or a halogen atom); and m is an integer of 0 to 3) and
(b) a group of the formula —$(CH_2)_p$—$R_b$ (wherein $R_b$ is a lower alkanoyl group, a hydroxy group, a cyano group or a mono- or di(lower alkyl)aminocarbonyl group, and p is an integer of 1 to 4); $R_2$ and $R_3$ are each a hydrogen atom, or either of them is a hydrogen atom and the other is a lower alkanoyl group, a lower alkoxycarbonyl group or an aralkyloxycarbonyl group, or together form a phthaloyl group; and $R_4'$ is a halogen atom, a hydroxy group, a lower alkylsulfonyloxy group or a phenylsulfonyloxy group which may be substituted (a substituent thereof is a lower alkyl group, a lower alkoxy group or a halogen atom)]. The compound of the Formula (IV) is the compound of the Formula (I) in which $R_4$ is a group other than a hydrogen atom.

Further, according to the present invention, provided is 7-substituted-L-tryptophan of the Formula (III):

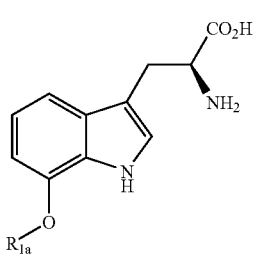

(wherein $R_{1a}$ is the same as described above).

BEST MODE FOR CARRYING OUT THE INVENTION

The respective atoms or groups constituting the compounds represented by (I), (II), (III) and (IV) according to the present invention commonly mean the following unless otherwise described.

The "lower alkyl group" means a linear or branched alkyl group having 1 to 6 carbon atoms, preferably 1 to 4 carbon atoms regardless of whether it is an independent group or a part of a particular group and includes, for example, methyl, ethyl, propyl, isopropyl, butyl, isobutyl, sec-butyl and tert-butyl. The "lower alkoxy group" is a group in which an alkyl part comprises the lower alkyl group described above and in which an oxygen atom is covalently bonded to the above alkyl, and specific examples thereof include methoxy, ethoxy, propoxy and isopropoxy. The "lower alkoxycarbonyl group" is a group formed from alkoxy having the lower alkyl group described above in an alkyl part and carbonyl, and specific examples thereof include methoxycarbonyl, ethoxycarbonyl, propoxycarbonyl, butoxycarbonyl and tert-butoxycarbonyl. The "lower alkanoyl group" is an acyl group formed from the lower alkyl group described above as an alkyl part and carbonyl, and specific examples thereof include acetyl and propionyl.

The "halogen" or "halogen atom" means usually fluorine, chlorine, bromine and iodine but in the definition of $R_4$ in Formula (I), it is particularly preferably iodine, bromine and chlorine.

The "phenyl group which may be substituted with lower alkyl, lower alkoxy, hydroxy or halogen" means a phenyl group which may be substituted with the same or different, up to four groups of the lower alkyl, lower alkoxy, halogen and hydroxy each described above, and capable of being given as specific examples thereof are phenyl, 4-methylphenyl, 4-methoxyphenyl, 2,6-dimethylphenyl, 3,5-dihydroxyphenyl, 2,3-dichlorophenyl and 2,6-dichlorophenyl. Accordingly, capable of being given as specific examples of $R_1$ in the case where $R_1$ is represented by the formula —$(CH_2)_p$—$R_b$ in Formula (I) and $R_b$ is the phenyl group described above are benzyl, phenethyl, 3-phenylpropyl, 4-phenylbutyl, 4-methylbenzyl and 4-methoxybenzyl. When $R_1$ is one of these groups, the corresponding compound can be subjected to biochemical conversion reaction, though described later in details, while holding such groups. Among these groups, particularly a benzyl group can readily be eliminated by hydrogenolysis and therefore is favorably converted to the other groups.

Specific examples of the "mono- or di-lower alkylaminocarbonyl group" include methylaminocarbonyl, dimethylaminocarbonyl, ethylaminocarbonyl, methylethylaminocarbonyl and diethylaminocarbonyl. Representative examples of $R_1$ in the case where $R_1$ is represented by the formula —$(CH_2)_p$—$R_b$ and $R_b$ is the mono- or di-lower alkylaminocarbonyl group described above include diethylaminocarbonylmethyl and dimethylaminocarbonylmethyl. When a part originating in the compound of Formula (I) according to the present invention has these groups, the final compound shows a good bioactivity in many cases (refer to WO96/16938).

Either of $R_2$ and $R_3$ can be a hydrogen atom, and the other can be the lower alkanoyl group, the lower alkoxycarbonyl group or the aralkyloxycarbonyl group (for example, benzyloxycarbonyl) each described above. In these cases, $R_2$, $R_3$ and a nitrogen atom to which they are bonded correspond to a so-called protected amino group in one group. Further, $R_2$ and $R_3$ can together form a phthaloyl group. In this case, $R_2$, $R_3$ and a nitrogen atom to which they are bonded correspond as well to a protected amino group in one group. When the compound of Formula (I) holds such protected amino group, the compound of Formula (I) is useful as a synthetic intermediate which can be derived into the other compounds via $R_2$ and/or $R_4$. On the other hand, when both of $R_2$ and $R_3$ are hydrogen atoms, the compound of Formula (I) is useful as a synthetic intermediate which can be derived into the other compounds via the free amino group.

—$CH_2$—$R_4$ in Formula (I) shall not be restricted and can be a group which is derived directly or indirectly from a carboxyl group. Accordingly, the group of $R_4$ can be hydroxy, lower alkylsulfonyloxy, lower alkyl, lower alkoxy or phenylsulfonyloxy which may be substituted with a halogen atom, a halogen atom and a hydrogen atom. The "lower alkyl" in these groups has the same meaning as described above. Accordingly, specific examples of alkylsulfonyloxy include methanesulfonyloxy, and specific examples of phenylsulfonyloxy which may be substituted with lower alkyl include p-toluenesulfonyloxy.

Compounds comprising combinations shown in the following Table 1 can be given as the compounds of Formula (I) comprising the preferred combinations of the respective groups explained above.

TABLE 1

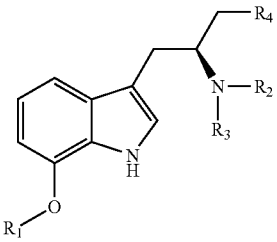

| Compound No. | $R_1$ | —$NR^2R^3$ |
|---|---|---|
| | $R_4$ = OH | |
| 1 | Bz- | —$NH_2$ |
| 2 | Bz- | —NPht |
| 3 | Bz- | —NHCOO$^t$Bu |
| 4 | $Et_2NCOCH_2$— | —$NH_2$ |
| 5 | $Et_2NCOCH_2$— | —NPht |
| 6 | $Et_2NCOCH_2$— | —NHCOO$^t$Bu |
| 7 | $PhCH_2CH_2$— | —$NH_2$ |
| 8 | $PhCH_2CH_2$— | —NPht |
| 9 | $PhCH_2CH_2$— | —NHCOO$^t$Bu |
| 10 | 4-$MePhCH_2$— | —$NH_2$ |
| 11 | 4-$MePhCH_2$— | —NPht |
| 12 | 4-$MePhCH_2$— | —NHCOO$^t$Bu |
| 13 | 4-$MeOPhCH_2$— | —$NH_2$ |
| 14 | 4-$MeOPhCH_2$— | —Pht |
| 15 | 4-$MeOPhCH_2$— | —NHCOO$^t$Bu |
| | $R_4$ = OTos | |
| 16 | Bz- | —$NH_2$ |
| 17 | Bz- | —NPht |
| 18 | Bz- | —NHCOO$^t$Bu |
| 19 | $Et_2NCOCH_2$— | —$NH_2$ |
| 20 | $Et_2NCOCH_2$— | —NPht |
| 21 | $Et_2NCOCH_2$— | —NHCOO$^t$Bu |
| 22 | $PhCH_2CH_2$— | —$NH_2$ |
| 23 | $PhCH_2CH_2$— | —NPht |
| 24 | $PhCH_2CH_2$— | —NHCOO$^t$Bu |
| 25 | 4-$MePhCH_2$— | —$NH_2$ |
| 26 | 4-$MePhCH_2$— | —NPht |
| 27 | 4-$MePhCH_2$— | —NHCOO$^t$Bu |
| 28 | 4-$MeOPhCH_2$— | —$NH_2$ |
| 29 | 4-$MeOPhCH_2$— | —NPht |
| 30 | 4-$MeOPhCH_2$— | —NHCOO$^t$Bu |
| | $R_4$ = I | |
| 31 | Bz- | —$NH_2$ |
| 32 | Bz- | —NPht |
| 33 | Bz- | —NHCOO$^t$Bu |
| 34 | $Et_2NCOCH_2$— | —$NH_2$ |
| 35 | $Et_2NCOCH_2$— | —NPht |
| 36 | $Et_2NCOCH_2$— | —NHCOO$^t$Bu |
| 37 | $PhCH_2CH_2$— | —$NH_2$ |

TABLE 1-continued

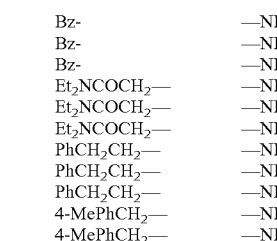

| Compound No. | $R_1$ | —$NR^2R^3$ |
|---|---|---|
| 38 | $PhCH_2CH_2$— | —NPht |
| 39 | $PhCH_2CH_2$— | —NHCOO$^t$Bu |
| 40 | 4-$MePhCH_2$— | —$NH_2$ |
| 41 | 4-$MePhCH_2$— | —NPht |
| 42 | 4-$MePhCH_2$— | —NHCOO$^t$Bu |
| 43 | 4-$MeOPhCH_2$— | —$NH_2$ |
| 44 | 4-$MeOPhCH_2$— | —NPht |
| 45 | 4-$MeOPhCH_2$— | —NHCOO$^t$Bu |
| | $R_4$ = H | |
| 46 | Bz- | —$NH_2$ |
| 47 | Bz- | —NPht |
| 48 | Bz- | —NHCOO$^t$Bu |
| 49 | $Et_2NCOCH_2$— | —$NH_2$ |
| 50 | $Et_2NCOCH_2$— | —NPht |
| 51 | $Et_2NCOCH_2$— | —NHCOO$^t$Bu |
| 52 | $PhCH_2CH_2$— | —$NH_2$ |
| 53 | $PhCH_2CH_2$— | —NPht |
| 54 | $PhCH_2CH_2$— | —NHCOO$^t$Bu |
| 55 | 4-$MePhCH_2$— | —$NH_2$ |
| 56 | 4-$MePhCH_2$— | —NPht |
| 57 | 4-$MePhCH_2$— | —NHCOO$^t$Bu |
| 58 | 4-$MeOPhCH_2$— | —$NH_2$ |
| 59 | 4-$MeOPhCH_2$— | —NPht |
| 60 | 4-$MeOPhCH_2$— | —NHCOO$^t$Bu |

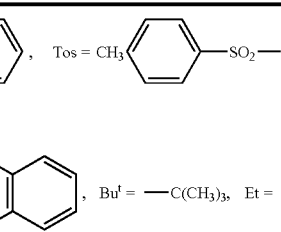

The compounds described above are provided as compounds which have at least one asymmetric carbon in a molecule and which are substantially optically pure. The term "substantially optically pure" means that the compounds having a specific configuration in which a carbon atom combined with a $NR_2R_3$ group is an asymmetric center have a purity of 90% or more, preferably 95% or more.

The substantially optically pure compound of Formula (I) described above can efficiently be obtained by reacting 7-substituted indole with serine in the presence of a tryptophan-synthesizing enzyme according to the present invention to produce corresponding L-7-substituted tryptophan (hereinafter referred to as a biochemical conversion step) and subjecting L-7-substituted tryptophan thus obtained which is used as a starting material to publicly known chemical reaction.

According to the biochemical conversion step described above, the conversion reaction is carried out in the presence of a tryptophan-synthesizing enzyme originating in microorganisms. The above term "in the presence of a tryptophan-synthesizing enzyme" means a system or an environment in which corresponding 7-substituted L-tryptophan can be prepared from 7-substituted indole of Formula (II) and L-serine:

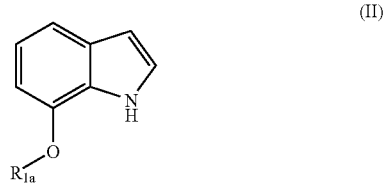

(II)

(wherein $R_{1a}$ is the same as described above) by virtue of the action of the tryptophan-synthesizing enzyme (or a tryptophan synthase: EC 4. 1. 99. 1.). Capable of being given as such system or environment is a culture of a microorganism producing a tryptophan-synthesizing enzyme or a cell lyzate originating in the culture, which has an activity for producing 7-benzyloxy-L-tryptophan from at least, for example, 7-benzyloxyindole and L-serine. Such activity may allow the forming reaction described above to resultingly proceed regardless of depending on the action of any of complex (for example, $\alpha_2\beta_2$, $\beta_2$ and the like) of the respective subunits in the tryptophan-synthesizing enzyme (or a tryptophan synthase: EC 4. 1. 99. 1.).

Microorganisms producing the culture described above shall no be restricted and include *Esherichia coli* W3110 trp AE1 trp R tna A (pSC101-trp 115) (FERM P-17433; domestically deposited to the following institute effective as of Jun. 28, 1999) (refer to Japanese Patent Application Laid-Open No. 140891/1984; this bacterial strain was transferred to National Institute of Bioscience and Human-Technology National Institute of Advanced Industrial Science and Technology, 1–3, Higashi 1-chome, Tsukuba city, Ibaraki prefecture 305–8566, Japan effective as of Feb. 7, 2001 to obtain a deposit number of FERM BP-7444) and in addition thereto, publicly known recombinant microorganism used for a producing L-tryptophan described above.

A method for producing a recombinant organism having the activity described above (incorporating a gene coding a tryptophan synthase originating in microorganisms into a suitable vector and then subjecting the respective hosts to transformation) is known to a person having an average skill in the art, and capable of being given as patent literatures which can be referred to are, for example, Japanese Patent Application Laid-Open No. 255082/1990, Japanese Patent Application Laid-Open No. 265892/1989 and Japanese Patent Application Laid-Open No. 211319/1994. Accordingly, a microorganism which can produce corresponding L-7-substituted tryptophan from 7-substituted indole of Formula (II) described above and L-serine shall not be restricted to microorganisms in which a gene coding a tryptophan-synthesizing enzyme used for a specific genus and recombination has specific origin. However, capable of being given as a suitable organism is *Esherichia coli* W3110 trp AE1 trp R tna A (pSC101-trp 115) (FERM BP-7444). This microorganism is lacking in a tryptophanase activity, and a plasmid containing a tryptophanase operon can very stably be present in a host fungus and therefore is easily handled. The present invention shall be explained below by citing the above FERM BP-7444 strain (hereinafter referred to as an AGX-1757 strain) for the purpose of simplify explanation. In such biochemical conversion step, a $R_{1a}$ group in 7-substituted indole of the Formula (II) represents preferably the formula $-(CH_2)_p-R_b'$ considering chemical treatment thereafter.

A cultured substance is prepared by culturing the AGX-1757 strain on a culture medium and a culture condition which are usually used for culturing *E. coli*. 7-Substituted indole of Formula (II) and L-serine may be contained in advance in a culture medium, and in general, a microorganism is preferably added to a cultured substance up to a log phase or a steady phase and then incubated. The culture described above can be carried out on a culture medium containing a carbon source, a nitrogen source, inorganic salts and the like which are conventionally known and usually used. Used as the carbon source are, for example, glucose, glycerol, fructose, sucrose and blackstrap molasses, and used as the nitrogen source are, for example, ammonia, ammonium sulfate, ammonium chloride and ammonium nitrate. They each are used alone or in a mixture. Further, used as the inorganic salts are, for example, potassium monohydrogenphosphate, potassium dihydrogenphosphate and magnesium sulfate. In addition thereto, capable of being added to the culture medium are nutrients including peptone, meat extract, enzyme extract, corn steep liquor, cazaminoic acid and various vitamins such as biotin and thiamin.

Culturing can be carried out usually at a culture temperature of 20 to 50° C. under an aerobic condition of aerobic stirring and shaking. The pH in the middle of culturing can be set to the vicinity of 5 to 10, preferably 7 to 8, and the pH during culturing can be controlled by adding an acid or an alkali.

In general, 7-substituted indole of Formula (II) and L-serine are preferably added to a culture at the same time, but it shall not be restricted thereto. When a pH of a culture liquid exceeds 8.0 or after it is controlled to such level, the raw materials to be reacted are preferably added. Incubation after adding them can be carried out at the same temperature as the culture temperature described above while aerobically stirring. An addition proportion of 7-substituted indole of Formula (II) to L-serine is 1:5 to 2:1, preferably 1:1.1 in terms of a mole ratio. In this case, a concentration of 7-substituted indole added shall not be restricted as long as it does not exert an adverse effect on the intended conversion reaction, and it is preferably 5 to 50 mM.

In another method, mycelium are taken from the culture described above, and these mycelium themselves or a crude enzyme preparation prepared from the mycelium are sealed in a system by making use of a membrane to react 7-substituted indole with L-serine described above.

L-7-substituted tryptophan produced by the conversion reaction described above can be obtained in the form of a pure product by a conventionally known separation-purifying method of tryptophan.

The foregoing process for producing L-7-substituted tryptophan not only constitutes one embodiment of the present invention but also is one essential step in producing the compound of Formula (I).

The compound of Formula (I) is produced via a chemical synthetic conversion reaction in which a reaction method itself is publicly known using the L-7-substituted tryptophan produced above as a starting material. The typical conversion reaction is shown in the following reaction scheme.

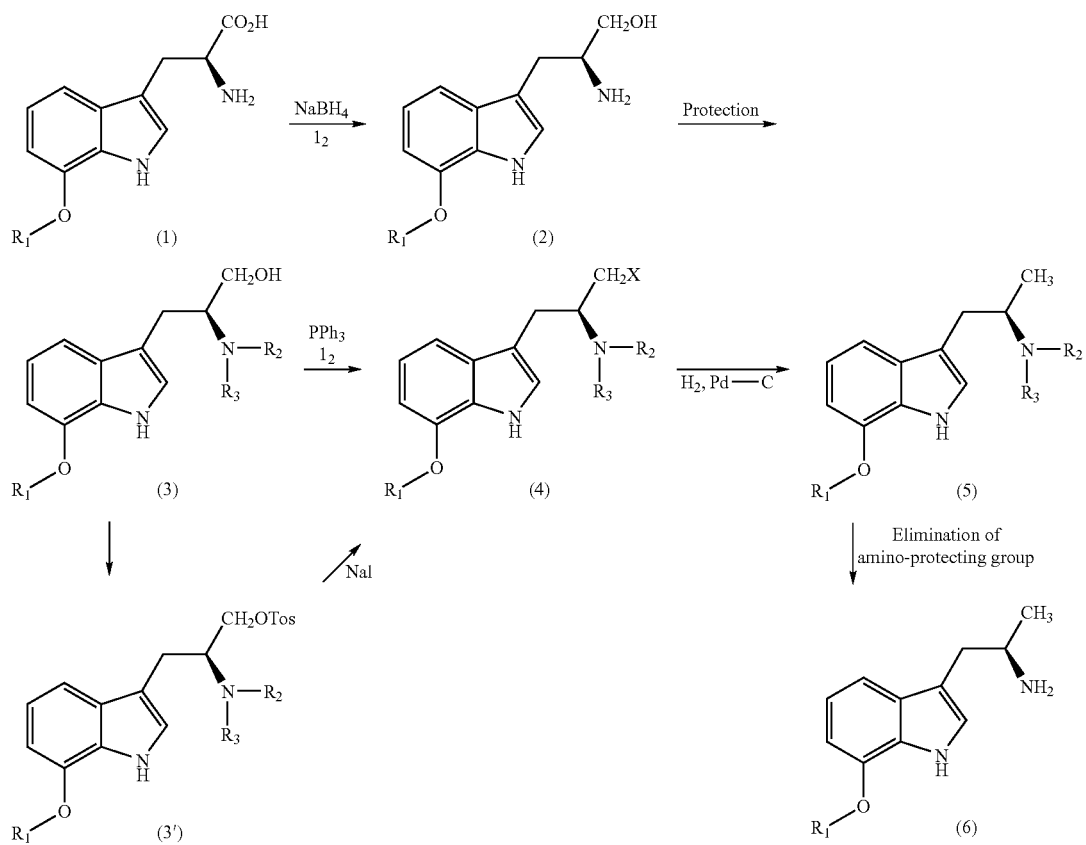

R$_1$; Me, Bzl, Et$_2$NCOCH$_2$, and the like
R$_2$, R$_3$; Pht, (COOBu$^t$, H), (Tos, H)

A reaction for reducing a compound (1) to a compound (2) is carried out in a solvent using a reducing agent such as diborane, lithium aluminum hydride and the alkoxy complexes, or sodium borohydride to which transition metal salts, aluminum chloride, boron trifluoride, phosphorus oxychloride, iodine or carboxylic acid (for example, acetic acid and trifuoroacetic acid) is added. The present reducing reaction is carried out in a solvent including ethers such as diethyl ether, tetrahydrofuran, dimethoxyethane, dioxane and diglyme, toluene, chloroform and methylene chloride, and the solvent is suitably selected depending on the kind of the reducing agent used. The reaction temperature is varied depending on the kind of the reducing agent, and it is usually about 0° C. to about 160° C., preferably about 10° C. to about 80° C.

A protective group for an amino group of the compound (2) includes ethoxycarbonyl, t-butoxycarbonyl, acetyl, benzoyl, trifluoroacetyl, benzyloxycarbonyl and phthaloyl. The reaction can be carried out according to a conventional method, and it is carried out by reacting with a reagent of the intended protective group in a suitable solvent. The solvent is selected depending on the kind of the protective group, and the reaction temperature is usually about −20° C. to about 200° C., preferably about 0° C. to about 150° C.

A hydroxyl group of the compound (3) is halogenated by direct halogenation using a halogenating agent such as thionyl chloride and thionyl bromide or direct halogenation in the presence of triphenylphosphine. Also, the hydroxyl group of the compound (3) is once turned into sulfonyloxy to form a compound (3'), and it is further reacted with alkali halide, whereby it can be halogenated as well. These reactions are carried out usually in suitable solvents, and the solvents used have to be suitably selected depending on the kind of the reaction reagents. They include, for example, aromatic hydrocarbons such as benzene, toluene and xylene, ethers such as diethyl ether, tetrahydrofuran and dioxane, halogenated hydrocarbons such as methylene chloride and chloroform, ketones such as acetone and methyl ethyl ketone, ethyl acetate, acetonitrile, dimethylforamide and dimethylsulfoxide. These solvents each are used alone or in a mixture of two or more kinds thereof.

The present reaction is carried out, if necessary, in the presence of a base, and specific examples of the base include alkali hydroxides such as sodium hydroxide and potassium hydroxide, alkali carbonates such as sodium carbonate and potassium carbonate, alkali bicarbonates such as sodium bicarbonate and potassium bicarbonate and organic bases such as triethylamine, tributylamine, diisopropylethylamine and N-methylmorpholine. The reaction temperature is usually about −20° C. to about 200° C., preferably about 0° C. to about 150° C.

A reducing reaction of a compound (5) in which halogen is substituted with hydrogen from a compound (4) is carried out by reacting them in a suitable solvent in the presence of a palladium on carbon catalyst and hydrogen or a hydrogen-donating substance such as ammonium formate and cyclohexene. Used as the solvent are, for example, alcohols such as ethanol and methanol, water, acetic acid, tetrahydrofuran, dioxane, acetone, ethyl acetate, acetonitrile and dimethylforamide. The reaction temperature is usually about 0° C. to about 150° C., and the reaction is carried out at an atmospheric pressure or under applied pressure.

A deprotecting reaction of the compound (5) is carried out by hydrolysis, hydrogenolysis or reaction with hydrazine (the protective group is phthaloyl). Deprotecting by hydrolysis can be carried out by a conventional method, and it is carried out, for example, by bringing the protective group into contact with water in a suitable solvent on an acid or basic condition. Used as the solvent are, for example, alcohols such as ethanol and methanol, water, tetrahydrofuran, dioxane, acetone, acetonitrile, dimethylformamide or a mixed solvent thereof. Specific examples of the acid include mineral acids such as hydrochloric acid, hydrobromic acid, hydroiodic acid and sulfuric acid and organic acids such as formic acid, acetic acid, trifluoroacetic acid, p-toluenesulfonic acid and methanesulfonic acid. Specific examples of the base include alkali hydroxides such as sodium hydroxide and potassium hydroxide and alkali carbonates such as sodium carbonate and potassium carbonate. The reaction temperature is usually about 0° C. to about 150° C.

Deprotecting by hydrogenolysis can be carried out by a conventional method, and to be specific, it is carried out by the method described above. Elimination of a phthaloyl group is carried out usually by reacting with hydrazine hydrate in a solvent including alcohols such as ethanol and methanol. The reaction temperature is usually about 50° C. to about 100° C.

An exchange reaction of $R_1$ is carried out by reaction of a 7-hydroxyindole derivative [obtained by catalytically reducing $R_{1a}$ which is a benzyl group allowed to be substituted $(-(CH_2)_m-CHR_a'R_{aa}'$ (wherein m=0, $R_a'$=a hydrogen atom, $R_{aa}'$=a phenyl group allowed to be substituted) or a benzhydryl group allowed to be substituted $(-(CH_2)_m-CHR_a'R_{aa}'$ (wherein m=0, $R_a'$=$R_{aa}'$=a phenyl group allowed to be substituted)] with a corresponding alkyl derivative. This reaction is carried out in a solvent or in the absence of a solvent. The solvent used has to be suitably selected depending on the kind of the raw material compounds, and it includes, for example, aromatic hydrocarbons such as benzene, toluene and xylene, ethers such as diethyl ether, tetrahydrofuran and dioxane, halogenated hydrocarbons such as methylene chloride and chloroform, alcohols such as ethanol and isopropanol, ketones such as acetone and methyl ethyl ketone, ethyl acetate, acetonitrile, dimethylformamide, dimethylsulfoxide and ethylene glycol. These solvents each are used alone or in a mixture of two or more kinds thereof. The present reaction is carried out, if necessary, in the presence of a base, and specific examples of the base include alkali hydroxides such as sodium hydroxide and potassium hydroxide, alkali carbonates such as sodium carbonate and potassium carbonate, alkali bicarbonates such as sodium bicarbonate and potassium bicarbonate and organic bases such as triethylamine, tributylamine, diisopropylethylamine and N-methylmorpholine. The reaction temperature is usually about −20° C. to about 200° C., preferably about 20° C. to about 150° C.

The present invention shall further be explained with reference to specific examples.

EXAMPLE 1

Production of L-7-benzyloxytryptophan

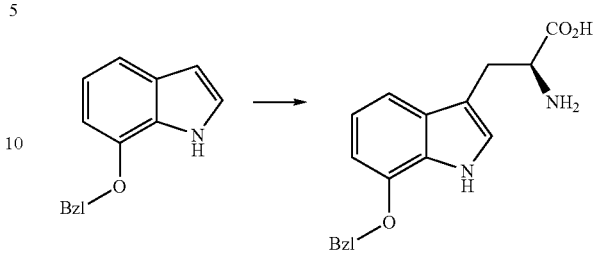

(i) Culture of *E. coli*

An *Esherichia coli* AGX-1757 (FERM BP-7444) strain was cultured on the following conditions using a jar fermentor having a volume of 3 liter.

Conditions:

| | |
|---|---|
| Cazaminoic acid | 2.5 g |
| Ammonium sulfate | 10 g |
| Enzyme extract | 1 g |
| Monopotassium phosphate | 2 g |
| Magnesium sulfate 7 hydrate | 1 g |
| Ferrous sulfate 7 hydrate | 10 mg |
| Defoaming agent Adekapulronic | 75 μl |
| Distilled water | 900 ml |
| 60% Glucose aqueous solution | 100 ml |
| pH | 7.0 |

Culturing was carried out at a temperature of 37° C. Aerobic stirring was carried out during culturing so that a dissolved oxygen concentration does not become rate-determining. A pH of the culture solution was reduced until 20 hours since starting culture, and therefore a sodium hydroxide solution was always added to maintain pH at 7.0.

(ii) Conversion Reaction

When 20 hours passed since starting the culturing described above, glucose contained in the culture medium spent up, and a rise in the pH and the dissolved oxygen concentration was observed. When the pH exceeded 8.0, 10 g (12.5% methanol solution) of 7-benzyloxyindole and 5.2 g (25% aqueous solution) of L-serine were added to the culture solution to carry out the conversion reaction while aerobically stirring at 37° C. After reaction for 4 hours, a sodium hydroxide aqueous solution was added to control the pH to 11.3, and the mycelium was separated by centrifugal filtering. A sulfuric acid solution was added to this filtrate to control the pH to 7, and the resulting precipitate was filtered and dried under reduced pressure to obtain a crude crystal of L-7-benzyloxytryptophan. This crude crystal was suspended in water, and a sodium hydroxide aqueous solution was added thereto to dissolve it. Then, sulfuric acid was added similarly to precipitate it. This precipitate was filtered and dried to obtain 9.7 g of the captioned compound.

Melting point: 213 to 218° C. (decomposed) Angle of rotation: +1.8° (c1.0, 0.05M NaOH)

FABMS(m/z): 311 [(M+H)$^+$] NMR(DMSO-d6) δ 2.89 (1H, dd, J=8.8, 15.0 Hz), 5.25(2H, s), 6.73(1H, d, J=7.7 Hz), 6.88(1H, dd, J=7.7, 7.7 Hz), 7.14(1H, dd, J=7.7, 7.7 Hz), 7.14(1H, d, J=7.7 Hz), 7.34(1H, d, J=7.7 Hz), 7.40(2H, dd, J=7.0, 7.7 Hz), 7.55(2H, d, J=7.0 Hz), 10.97(1H, broad)

2H is superposed on 3.3 ppm DHO.

In analysis using CHIRALPAK AD (mobile phase: n-hexane/ethanol/trifluoroacetic acid=90/10/0.2), only a peak of an L isomer was detected, and a D isomer was not observed.

EXAMPLE 2

Production of L-7-diethylaminocarbonylmethyloxytryptophan

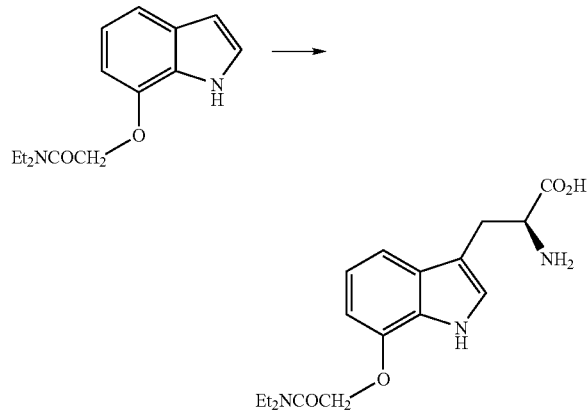

The conversion reaction described in Example 1 was substantially repeated to obtain a reaction liquid, except that 0.5 g (10% methanol solution) of 7-diethylaminocarbonylmethyloxyindole and 5.0 g (25% aqueous solution) of L-serine were substituted for 7-benzyloxyindole and L-serine used in Example 1 and that used was a culture solution prepared by controlling a pH of one liter of a culture solution obtained after culturing for 22 hours to 9.0 by adding aqueous ammonia. A supernatant obtained by centrifuging this solution was passed through a column filled with Diaion HP-20 (manufactured by Mitsubishi Chemical Co., Ltd.) and adsorbed thereon, and then it was eluted by 30% methanol to obtain a fraction corresponding to the product, which was dried up. The dried matter was dissolved in 50% acetonitrile, and then the solution was fractionated through fractional HPLC [column Inertsil PREP-ODS (GASUKURO KOGYO); mobile phase 20% acetonitrile, isocratic eluted, detection: UV254 nm] to obtain a product-containing fraction, and it was dried up to obtain 0.5 g of the intended compound. The compound thus obtained was identified to be 7-diethylaminocarbonylmethyloxytryptophan by means of $^1$H-NMR and FAB mass spectrum.

EXAMPLE 3

Preparation of (S)-7-benzyloxy-3-(2-amino-3-hydroxypropyl)indole

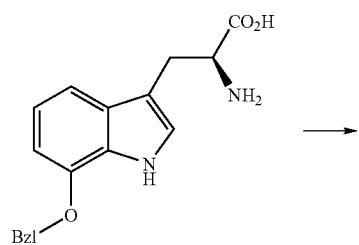

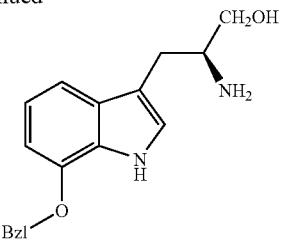

L-7-Benzyloxytryptophan 50 g was suspended in 400 ml of tetrahydrofuran (THF), and 15 g of sodium borohydride was added thereto at 0° C., followed by dropwise adding a solution of 40 g of iodine in THF (100 ml) in 40 minutes. After refluxing for 2 hours by heating, the solution was cooled to 0° C., and 25 ml of methanol and 500 ml of hydrochloric acid (2 mol/l) were dropwise added thereto. Then, the solvent was evaporated under reduced pressure until the solution amount became about a half. The solution was cooled to 0° C., and 600 ml of a sodium hydroxide aqueous solution (2 mol/l) was dropwise added thereto. The solution was extracted with 1000 ml of ethyl acetate, and the organic layer was washed with a saturated brine. The resulting extract was dried over anhydrous sodium sulfate, and then the solvent was evaporated under reduced pressure to give 45.2 g of the title compound.

FABMS(m/z): 297 [(M+1)] NMR(CDCl3) δ: 2.70(1H, dd, J=8.0, 14.3 Hz), 2.92(1H, dd, J=4.7, 14.3 Hz), 3.25(1H, m), 3.42(1H, dd, J=7.0, 10.6 Hz), 3.68(1H, dd, J=2.3, 10.6 Hz), 5.20(2H, s), 6.73(1H, d, J=7.7 Hz), 6.9–7.1(2H, m), 7.22(1H, d, J=7.7 Hz), 7.3–7.5(5H, m), 8.29(1H, broad)

EXAMPLE 4

Preparation of (S)-7-benzyloxy-3-(3-hydroxy-2-phthalimidopropyl)indole

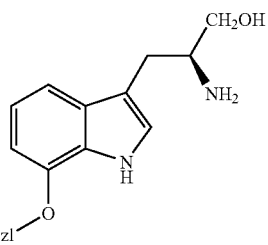

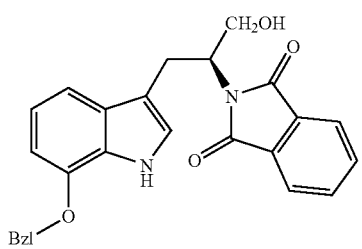

(S)-7-Benzyloxy-3-(2-amino-2-hydroxypropyl)indole 45.2 g was dissolved in 150 ml of N-dimethylformamide (DMF), and 25 ml of triethylamine and 29 g of phthalic anhydride were added thereto, followed by stirring the solution at 130° C. For 2.5 hours. The solution was cooled to 0° C. And then diluted with 300 ml of toluene, and it was washed with 200 ml of hydrochloric acid (0.1 mol/l). The separated aqueous layer was further extracted twice with 100 ml of toluene. Ethyl acetate 200 ml was added to the combined toluene layer, and the organic solution was washed successively with twice a 10% sodium thiosulfate aqueous solution, a sodium hydrogencarbonate aqueous solution, and a saturated brine. The extract thus obtained was dried over anhydrous sodium sulfate, and then the solvent was evaporated under reduced pressure until the whole amount was reduced to 400 ml. This solution was left standing one night to collect by filtration the resulting crystal, and then it was washed with 300 ml of toluene and 300 ml of hexane and dried to give 35.5 g of the title compound.

FABMS(m/z): 426 [(M)+] NMR(CDCl3)δ: 3.32(1H, dd, J=7.3, 15.0 Hz), 3.39(1H, dd, J=7.3, 15.0 Hz), 3.94(1H, dd, J=3.3, 12.1 Hz), 4.10(1H, dd, J=6.7, 12.1 Hz), 4.76 (1H, dd dd, J=3.3, 6.7, 7.3, 7.3 Hz), 5.17(2H, s), 6.70(1H, d, J=8.1 Hz), 7.01(1H, dd, J=8.1, 8.1 Hz), 7.04(1H, d, J=2.6 Hz), 7.3–7.5(6H, m), 7.70(2H, dd, J=2.9, 5.5 Hz), 7.80(2H, dd, J=2.9, 5.5 Hz), 8.24 (1H, broad)

EXAMPLE 5

Preparation of (S)-7-benzyloxy-3-(2-phthalimide-3-p-toluene sulfonyloxy propyl)indole

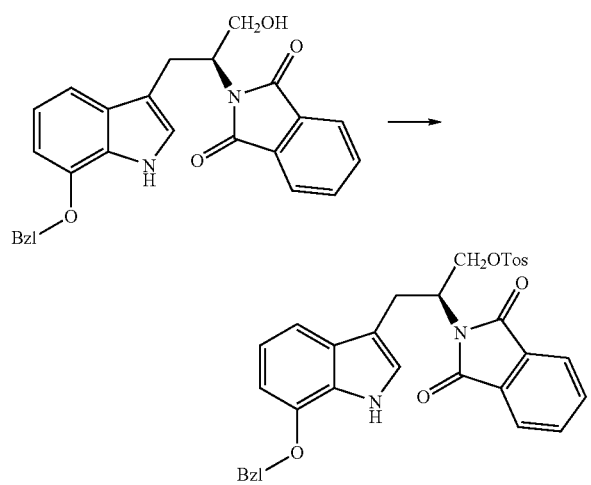

(S)-7-Benzyloxy-3-(3-hydroxy-2-phthalimidopropyl)indole 3.8 g was dissolved in 9.5 ml of pyridine, and 2.1 g of p-toluenesulfonyl chloride was added thereto, followed by stirring the solution at room temperature for 2 hours. The solution was diluted with 50 ml of ethyl acetate, and it was washed successively with water, three times with hydrochloric acid (2 mol/l) and a saturated brine. The extract thus obtained was dried on anhydrous sodium sulfate, and then the solvent was evaporated under reduced pressure to give 4.68 g of the title compound.

FABMS(m/z): 580[(M)+] NMR(CDCl3) δ: 2.32(3H, s), 3.24(1H, dd, J=8.1, 15.2 Hz), 3.30(1H, dd, J=8.1, 15.2 Hz), 4.32(1H, dd, J=3.7, 10.3 Hz), 4.78(1H, dd, J=10.3, 10.3 Hz), 4.8–4.9(1H, m), 5.15(2H, s), 6.68(1H, d, J=7.7 Hz), 6.92 (1H, d, J=2.5 Hz), 6.97(1H, dd, J=7.7, 7.7 Hz), 7.10(1H, d, J=8.0 Hz), 7.13(1H, d, J=8.0 Hz), 7.3–7.5(5H, m), 7.61(2d, J=8.4 Hz), 7.6–7.8(4H, m), 8.19 (1H, broad)

EXAMPLE 6-1

Preparation of (S)-7-benzyloxy-3-(3-iodo-2-phthalimide propyl)indole

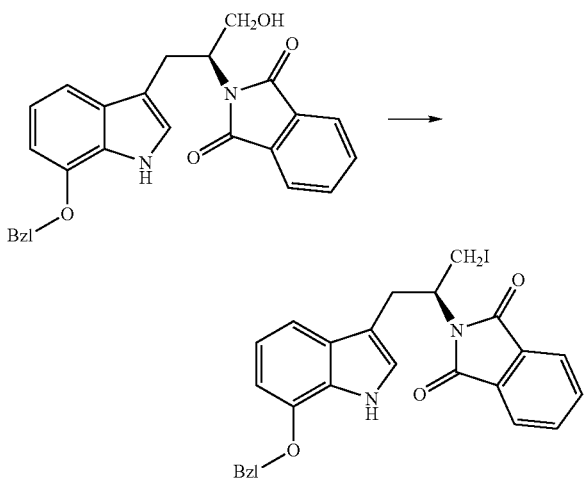

(S)-7-Benzyloxy-3-(3-hydroxy-2-phthalimidopropyl)indole 35.45 g was dissolved in 177 ml of THF, and 14.3 g of imidazole, 26.4 g of triphenylphosphine and 42.6 g of iodine were added thereto, followed by stirring the solution at 60° C. For 3 hours. The reaction solution was cooled down and then diluted with 1,060 ml of ethyl acetate, and it was washed successively with a saturated sodium hydrogencarbonate aqueous solution, twice a 10% sodium thiosulfate aqueous solution and a saturated brine. The extract thus obtained was dried over anhydrous sodium sulfate and then concentrated under reduced pressure, and 350 ml of methanol was added to the resulting residue. The solution was heated to reflux at 80° C., and a white crystal formed was collected by filtration and washed with 106 ml of methanol, followed by drying to obtain 30.06 g of the title compound.

FABMS(m/z): 537 [(M+H)+] NMR (CDCl3) δ: 3.44(2H, d, J=8.4 Hz), 3.56(1H, dd, J=4.8, 10.4 Hz), 4.03(1H, dd, J=10.4, 10.4 Hz), 4.84(1H, ddt, J=4.8, 8.4, 10.4 Hz), 5.16 (2H, s), 6.70(1H, d, J=7.7 Hz), 6.99(1H, d, J=2.6 Hz), 7.01(1H, dd, J=7.7, 7.7 Hz), 7.26(1H, d, J=8.1 Hz), 7.3–7.5 (5H, m), 7.69(2H, dd, J=2.9, 5.5 Hz), 7.80(2H, dd, J=2.9, 5.5 Hz), 8.23(1H, broad)

EXAMPLE 6-2

Preparation of (S)-7-benzyloxy-3-(3-iodo-2-phthalimide propyl)indole

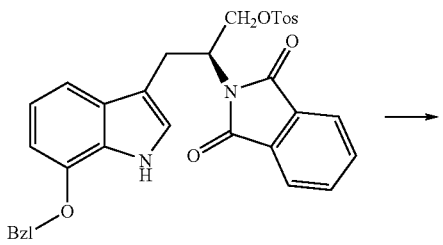

-continued

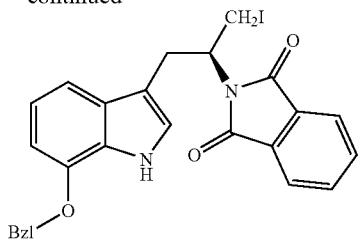

(S)-7-Benzyloxy-3-(2-phthalimide-3-p-toluenesulfonyloxypropyl)indole 4.68 g was dissolved in 10 ml of DMF, and 2.0 g of sodium iodide was added thereto, followed by stirring the solution at 120° C. For 2 hours. The reaction solution was cooled down and then diluted with 30 ml of toluene, and it was washed successively with water and a saturated brine. The extract thus obtained was dried over anhydrous sodium sulfate and then concentrated under reduced pressure. The residue was purified by silica gel column chromatography to give 3.21 g of the title compound.

EXAMPLE 7

Preparation of (R)-7-benzyloxy-3-(2-phthalimidopropyl)indole

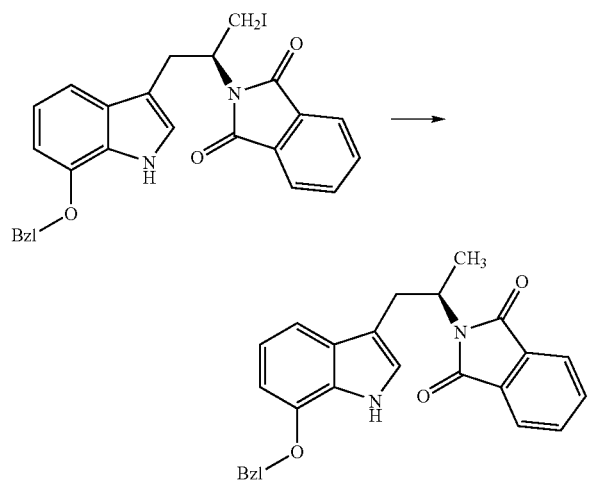

A 10% palladium on carbon catalyst (content 50%) 4.00 g was suspended in 200 ml of DMF, and 20.00 g of (S)-7-benzyloxy-3-(3-iodo-2-phthalimidopropyl)indole was added thereto. Added while stirring were 8.00 g of potassium carbonate and 6.00 g of ammonium formate, the suspension was heated in an oil bath of 85° C. For one hour. After cooling down, the catalyst was filtered off, and the filtrate was diluted with ethyl acetate. Then, water was added thereto, and the organic layer was separated. The organic layer was washed in order with a 10% sodium thiosulfate aqueous solution, a sodium hydroxide aqueous solution, hydrochloric acid and a saturated sodium chloride aqueous solution, and then it was dried, filtered and concentrated under reduced pressure, whereby 12.16 g of the title compound was obtained in the form of a yellow amorphous solid shaped substance.

FABMS(m/z): 410 [(M)⁺] NMR (CDCl3) δ: 1.54(3H, d, J=7.0 Hz), 3.23(1H, dd, J=7.3, 14.7 Hz), 3.46(1H, dd, J=8.5, 14.7 Hz), 4.77(1H, ddd, J=7.0, 7.3, 8.5 Hz), 5.12(2H, s), 6.68(1H, d, J=7.7 Hz), 6.96(1H, d, J=2.6 Hz), 7.00(1H, dd, J=7.7, 8.1 Hz), 7.29(1H, d, J=8.1 Hz), 7.30–7.45(5H, m), 7.62–7.66 (2H, m), 7.73–7.77(2H, m), 8.18(1H, broad)

EXAMPLE 8

Preparation of (R)-7-hydroxy-3-(2-phthalimidopropyl)indole

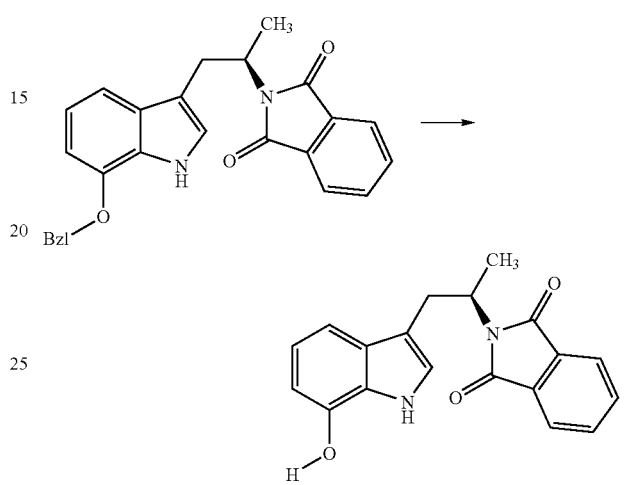

(R)-7-Benzyloxy-3-(2-phthalimidopropyl)indole 12.16 g was dissolved in 400 ml of ethanol, and a water 100 ml suspension of a 10% palladium on carbon catalyst (content 50%) 4.00 g prepared separately was added thereto. Ammonium formate 6.00 g was added thereto while stirring, and the suspension was heated in an oil bath of 95° C. For one hour. After cooling down, the catalyst was filtered off, and the filtrate was concentrated under reduced pressure. Acetone was added to the residue, and a deposited salt was filtered off. The filtrate was concentrated under reduced pressure, whereby 10.27 g of a residue containing the title compound was obtained.

FABMS(m/z): 320 [(M)⁺] NMR (CDCl3) δ: 1.55(3H, d, J=7.0 Hz), 3.23(1H, dd, J=7.0, 14.7 Hz), 3.46(1H, dd, J=8.8, 14.7 Hz), 4.77(1H, ddd, J=7.0, 7.0, 8.8 Hz), 5.71 (1H, broad), 6.54(1H, d, J=7.7 Hz), 6.90(1H, dd, J=7.7, 8.1 Hz), 6.93 (1H, d, J=2.2 Hz), 7.23(1H, d, J=8.1 Hz), 7.60–7.64 (2H, m), 7.71–7.76 (2H, m), 8.20(1H, broad)

EXAMPLE 9

Preparation of (R)-7-diethylaminocarbonylmethoxy-3-(2-phthalimidopropyl)indole

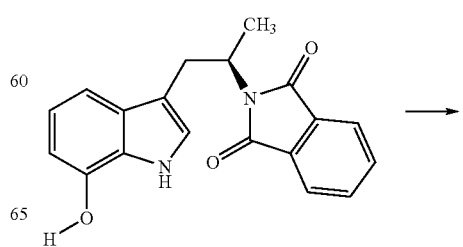

-continued

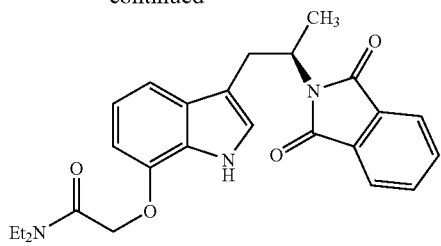

A residue 10.27 g containing (R)-7-hydroxy-3-(2-phthalimidopropyl)indole was dissolved in 200 ml of acetone, and 8.00 g of potassium carbonate was added thereto. After addition of N,N-diethylchloroacetamide 15.5 ml, the solution was heated to reflux in an oil bath of 80° C. For 3 hours. After cooling down 200 ml of water was added, and a deposited crystal was collected by filtration and washed with water, whereby 9.56 g of the title compound was obtained in the form of a pale yellowish white substance.

FABMS(m/z): 433 [(M)+] NMR (CDCl3) δ: 1.14(3H, d, J=7.1 Hz), 1.19(3H, d, J=7.1 Hz), 1.54(3H, d, J=7.0 Hz), 3.24(1H, dd, J=7.3, 14.7 Hz), 3.32(2H, q, J=7.1 Hz), 3.41 (2H, q, J=7.1 Hz), 3.45(1H, dd, J=8.1, 14.7 Hz), 4.75(2H, s), 4.77(1H, ddd, J=7.0, 7.3, 8.1 Hz), 6.62(1H, d, J=7.7 Hz), 6.97(1H, dd, J=7.7, 8.1 Hz), 7.00(1H, d, J=2.6 Hz), 7.33(1H, d, J=8.1 Hz), 7.63–7.66(2H, m), 7.73–7.76(2H, m), 9.34(1H, broad)

EXAMPLE 10

Preparation of (R)-7-diethylaminocarbonylmethyloxy-3-(2-aminopropyl)indole

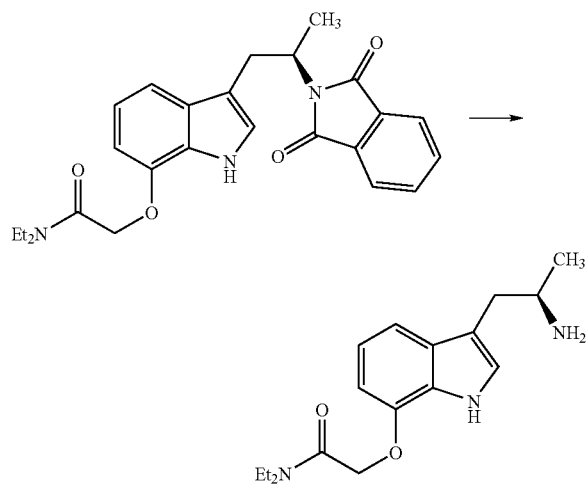

(R)-7-Diethylaminocarbonylmethyloxy-3-(2-phthalimidopropyl)indole 10.27 g was suspended in 100 ml of ethanol, and 2.5 ml of hydrazine monohydrate was added thereto. The suspension was heated to reflux in an oil bath of 85° C. For 3 hours. After cooling down, the resulting deposited insoluble materials were filtered off, and the filtrate was concentrated under reduced pressure. Ethyl acetate and a sodium hydroxide aqueous solution were added to the residue and distributed in liquid-liquid, and the organic layer was further washed with a sodium hydroxide aqueous solution and dried. The solution was evaporated under reduced pressure. The resulting residue was slowly crystallized, and dried under reduced pressure, whereby 6.90 g of the title compound was obtained in the form of a pale brownish white substance.

FABMS(m/z): 304 [(M+H)+] NMR (CD30D) δ: 1.12(3H, d, J=6.6 Hz), 1.17(3H, t, J=7.1 Hz), 1.24 (3H, t, J=7.1 Hz), 2.70(1H, dd, J=7.8, 14.2 Hz), 2.81(1H, dd, J=6.2, 14.2 Hz), 3.19(1H, ddd, J=6.2, 6.6, 7.8 Hz), 3.43–3.49(4H, m), 4.89 (2H, s), 6.64(1H, d, J=7.7 Hz), 6.91(1H, t, J=7.7 Hz), 7.07(1H, s), 7.19(1H, d, J=8.1 Hz)

EXAMPLE 11

Preparation of (S)-7-benzyloxy-3-(2-t-butoxycarbonylamino-3-hydroxypropyl)indole

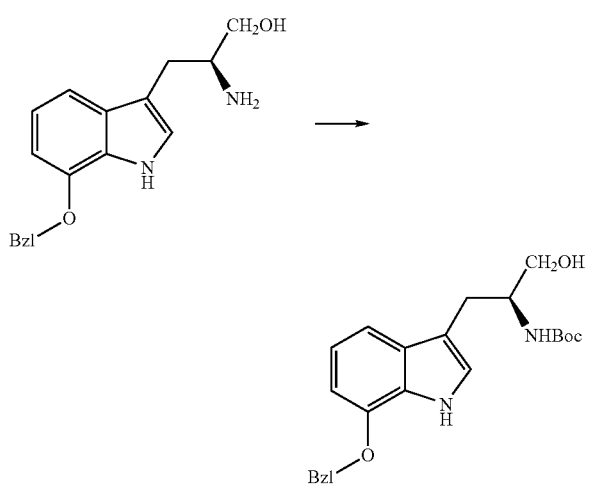

(S)-7-Benzyloxy-3-(2-amino-3-hydroxypropyl)indole 2.53 g was dissolved in 20 ml of 1,4-dioxane, and 20 ml of sodium hydroxide (1 mol/l) was added thereto. After addition of di-tert-butyl pyrocarboxylate 1.70 g, the mixture was stirred for 1.5 hour. The solution was diluted with 80 ml of ethyl acetate and then washed with 50 ml of water. The separated aqueous layer was further extracted with 100 ml of ethyl acetate, and the combined organic layer was washed with a saturated brine. The extract was dried over anhydrous sodium sulfate, and then the solvent was distilled off. The resulting residue was chromatographed on silica gel (hexane/ethyl acetate 1/1) to give 3.21 g of the title product.

FABMS(m/z): 396 [(M)+]

EXAMPLE 12

Preparation of (S)-7-benzyloxy-3-(2-t-butoxycarbonylamino-3-iodo)indole

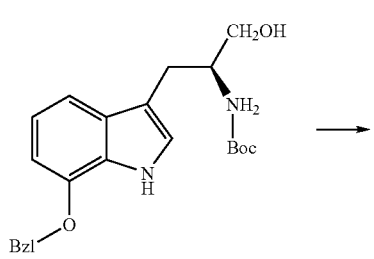

-continued

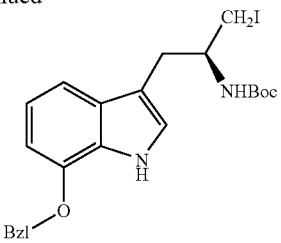

(S)-7-Benzyloxy-3-(2-t-butoxycarbonylamino-3-hydroxypropyl)indole 3.21 g was dissolved in 50 ml of THF, and 1.10 g of imidazole, 4.23 g of triphenylphosphine and 3.28 g of iodine were added thereto, followed by stirring the solution at room temperature for 25 minutes. A 10% sodium thiosulfate aqueous solution 50 ml was added thereto. The solution was stirred and extracted with 300 ml of ethyl acetate. The extract was washed successively with 100 ml of a 10% sodium thiosulfate aqueous solution was further added and distributed in liquid-liquid. The organic layer was washed with 100 ml of a 10% sodium thiosulfate aqueous solution and a saturated brine. The extract was dried over anhydrous sodium sulfate and concentrated to dryness under reduced pressure, to give 6.13 g of a residue containing the title compound was obtained.

FABMS(m/z): 506 [(M)+]

COMPARATIVE EXAMPLE

In this experiment, investigated was conversion from 7-benzyloxyindole to a corresponding tryptophan derivative using cultured substances of E. coli K-12 (ATCCC 14948) and AGX-1757 (FERM P-17433) as a tryptophan-synthesizing enzyme-producing microorganism.

The experimental conditions and the results are shown below respectively.

| Culture medium: | |
| --- | --- |
| K-12 strain | brain heart infusion culture medium (Difco) |
| AGX-1757 | brain heart infusion culture medium containing oxytetracycline monohydrochloride (Wako Pure Chemical) of 10 mg/l |

Culturing method:
Used was a 500 ml Erlenmeyer flask containing 50 ml of the culture medium having the composition described above.

A K12 strain grown on a slant was inoculated.

An AGX-1757 strain 200 μl of a froze culture stock was inoculated.

Cultured at 32° C. in a rotary shaker of 240 rpm.

| Conversion substrate: | |
| --- | --- |
| 7-benzyloxyindole | 125 g/l methanol solution |
| L-serine | 250 g/l aqueous solution |

Cultured for 22 hours. OD 660 nm values were 9.82 in the case of the K-12 strain and 7.86 in the case of the AGX-1757 strain. The culture broth had a pH of 8.54 in the case of the K-12 strain and 8.36 in the case of the AGX-1757 strain.

Conversion Reaction:
Added to these flasks were 4 ml of a 7-benzyloxyindole solution, 10 g/l and an L-serine solution, 10 g/l to carry out conversion reaction at 32° C. And 240 rpm.

Results:
A concentration of 7-benzyloxytryptophan contained in the culture solution was analyzed every 2 hours up to 6 hours by means of HPLC.

Formation of 7-benzyloxytryptophan was not observed in the K-12 strain. (Analysis sensitivity: 0.1 g/l or more)

In the AGX-1757 strain, formed were 2.33 g/l of 7-benzyloxytryptophan in 2 hours, 4.45 g/l in 4 hours and 6.93 g/l in 6 hours.

The results thereof are summarized in Table 2.

HPLC Conditions:
Column: Super-ODS (TOSO)
Elution: acetonitrile/water gradient elution
Temperature: 40° C.
Flow velocity: 2 ml/minute
Detection: UV 254 nm

TABLE 2

| Fungus strain | Time (hour) | 7BOT | 7BOI |
| --- | --- | --- | --- |
| K-12 | 2 | 0 | 10.2 |
| | 4 | 0 | 9.86 |
| | 6 | 0 | 10.1 |
| AGX-1757 | 2 | 2.33 | 7.05 |
| | 4 | 4.45 | 5.81 |
| | 6 | 6.93 | 5.86 |

7BOT: 7-benzyloxytryptophan
7BOI: 7-benzyloxyindole

INDUSRIAL APPLICABILITY

According to the present invention, provided is an efficient process for producing a specific optically active 7-substituted-3-(2-aminopropyl)indole compound. The above compound can be used as a synthetic intermediate for some fixed medicines. Accordingly, the present invention can be utilized, for example, in the medicine production industry.

What is claimed is:

1. A process for preparing an optically active indole derivative of the Formula (I):

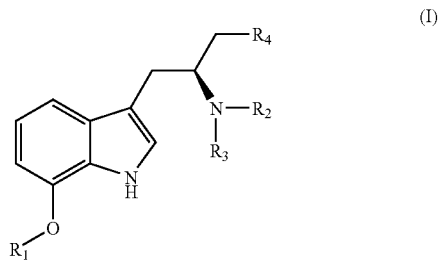

wherein $R_1$ is a hydrogen atom, a lower alkyl group or a group selected from the following (a) and (b):
(a) a group of the formula $-(CH_2)_m-CHR_aR_{aa}$ wherein $R_a$ is a hydrogen atom, a lower alkyl group, a lower alkoxycarbonyl group, a carboxyl group or a phenyl group which may be substituted by a lower alkyl group, a lower alkoxy group, a hydroxy group or a halogen atom; $R_{aa}$ is a lower alkoxycarbonyl group, a carboxyl group or a phenyl group which may be substituted by a lower alkyl group, a lower alkoxy group, a hydroxy group or a halogen atom; and m represents an integer of 0 to 3, and (b) a group of the formula —$(CH_2)_p$—$R_b$ wherein $R_b$ is a lower alkanoyl group, a hydroxy group, a cyano group or a mono- or di(lower alkyl)aminocarbonyl group, and p is an integer of 1 to 4;

$R_2$ and $R_3$ are each a hydrogen atom, or either of them is a hydrogen atom and the other is a lower alkanoyl group, a lower alkoxycarbonyl group or an aralkyloxycarbonyl group, or together form a phthaloyl group; and $R_4$ is a hydrogen atom, a halogen atom, a hydroxy group, a lower alkylsulfonyloxy group or a phenylsulfonyloxy group which may be substituted by a lower alkyl group, a lower ailcoxy group or a halogen atom, comprising:
(1) reacting L- or DL-serine with 7-substituted indole of the Formula (II):

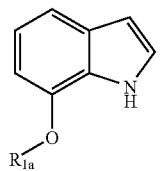
(II)

wherein $R_{1a}$ is a group (c) or (d) shown below:
(c) a group of the formula —$(CH_2)_m$—$CHR_a'R_{aa}'$ wherein $R_a'$ is a hydrogen atom, a lower alkyl group or a phenyl group which may be substituted by a lower alkyl group, a lower alkoxy group, a bydroxy group or a halogen atom; $R_{aa}'$ is a phenyl group which may be substituted by a lower alkyl group, a lower alkoxy group, a hydroxy group or a halogen atom; and m is an integer of 0 to 3, and
(d) a group of the formula —$(CH_2)_p$—$R_b'$ wherein $R_b'$ is a mono- or di(lower alkyl)aminocarbonyl group, and p is an integer of 1 to 4, in the presence of an effective amount of a tryptophan-synthesizing enzyme originating in E. coli to form a 7-substituted-L-tryptophan of the Formula (III):

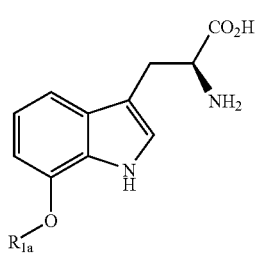
(III)

wherein $R_{1a}$ is the same as described above,
(2) chemically reducing the carboxyl group of the 7-substituted-L-tryptophan of Formula (III) thus formed to a methylol group,
(3) protecting the amino group of the compound of Formula (III),
(4) converting the hydroxy group of the methylol group to sulfonyl to form a corresponding lower alkylsulfonyloxy compound or a phenylsulfonyloxy compound which may be substituted by a lower alkyl group, a lower alkoxy group or a halogen atom, and halogenating the resultant compound with alkali halide, or directly halogenating the hydroxy group of the methylol group, optionally in the presence of triphenyiphosphine, to form a corresponding halide, (5) converting the sulfonyloxy compound or the halide obtained in (4) to methyl by hydrogenation in the presence of a palladium catalyst or using a metal hydride salt,
(6) subjecting the substituent of $R_1$ to exchange reaction when $R_1$ is the group (d) of the formula —$(CH_2)_p$—$R_b'$,
(7) eliminating the protective group of the amino group, and
(8) recovering the indole derivative of Formula (I).

2. The process according to claim 1, wherein $R_{1a}$ in the 7-substituted indole of Formula (II) is a group of the formula (c') —$(CH_2)_m$—$CHR_a''R_{aa}''$ wherein $R_a''$ is a hydrogen atom or a phenyl group which may be substituted by a lower alkyl group, a lower alkoxy group, a hydroxy group or a halogen atom; $R_{aa}'$ is a phenyl group which may be substituted by a lower alkyl group, a lower alkoxy group or a halogen atom; and m is an integer of 0 to 3.

3. The process according to claim 1, wherein the E. coli is W3110 trp AE1 trp R tna A (pSC101-trp I115) of accession no. FERM BP-7444.

4. A process for preparing 7-substituted L-tryptophan of the Formula (III):

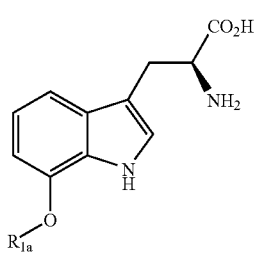
(III)

wherein $R_{11a}$ is defined below, which comprises reacting L- or DL-serine with 7-substituted indole of the Formula (II):

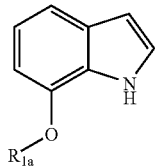
(II)

wherein $R_{1a}$ is a group (c) or (d) shown below:
(c) a group of the formula —$(CH_2)_m$—$CHR_a'R_{aa}'$ wherein $R_{a2}'$ is a hydrogen atom, a lower alkyl group or a phenyl group which may be substituted by a lower alkyl group, a lower alkoxy group, a hydroxy group or a halogen atom; $R_{aa}'$ is a phenyl group which may be substituted by a lower alkyl group, a lower alkoxy group, a hydroxy group or a halogen atom; and m is an integer of 0 to 3, and
(d) a group of the formula —$(CH_2)_p$—$R_b'$ wherein $R_b'$ is a mono- or di(Lower alkyl)aminocarbonyl group, and p is an integer of 1 to 4, in the presence of an effective amount of a tryptophan-synthesizing enzyme originating in E. coli, and recovering the 7-substituted L-tryptophan of Formula (III).

5. The process according to claim 4, wherein the E. coli is W3110 trpAE1 trp R tna A (pSC101-trp I15) of accession no. FERM BP-7444.

* * * * *